United States Patent [19]

Gilis et al.

[11] Patent Number: 5,405,642
[45] Date of Patent: Apr. 11, 1995

[54] METHOD OF HIGHLIGHTING INTAGLIATIONS IN TABLETS

[75] Inventors: Paul M. V. Gilis, Beerse; Valentin F. V. De Condé, Lommel, both of Belgium

[73] Assignee: Janssen Pharmaceutica N.V., Beerse, Belgium

[21] Appl. No.: 94,137
[22] PCT Filed: Feb. 14, 1992
[86] PCT No.: PCT/EP92/00358
§ 371 Date: Jul. 30, 1993
§ 102(e) Date: Jul. 30, 1993
[87] PCT Pub. No.: WO92/15288
PCT Pub. Date: Sep. 17, 1992

[30] Foreign Application Priority Data

Feb. 27, 1991 [EP] European Pat. Off. ........... 91200417

[51] Int. Cl.$^6$ ................................................ A61K 9/44
[52] U.S. Cl. .................... 427/2.23; 424/467; 424/476
[58] Field of Search ................ 427/3; 424/467, 476

[56] References Cited

U.S. PATENT DOCUMENTS

| | | | |
|---|---|---|---|
| 3,125,490 | 3/1964 | Hershberg | 167/82 |
| 3,436,453 | 4/1969 | Vincent, Jr. et al. | 424/467 |
| 3,539,380 | 11/1970 | Johnson | 117/100 |
| 4,522,840 | 6/1985 | Corfield et al. | 427/3 |
| 4,576,646 | 3/1986 | Brancq et al. | 106/163.1 |
| 4,661,367 | 4/1987 | Forse et al. | 427/3 |
| 4,665,648 | 5/1987 | Brancq et al. | 47/57.6 |
| 4,720,378 | 1/1988 | Forse et al. | 424/467 |
| 4,786,504 | 11/1988 | Forse et al. | 424/467 |
| 5,002,775 | 3/1991 | Toya et al. | 424/467 |
| 5,006,362 | 4/1991 | Hilborn | 427/3 |
| 5,098,715 | 3/1992 | McCabe et al. | 427/3 |

FOREIGN PATENT DOCUMENTS

| | | | |
|---|---|---|---|
| 1178853 | 12/1984 | Canada | 427/3 |
| 0088556 | 9/1983 | European Pat. Off. | |
| 0096982 | 12/1983 | European Pat. Off. | |
| 0133827 | 3/1985 | European Pat. Off. | |
| 0060023 | 9/1992 | European Pat. Off. | |
| 58-192819 | 1/1983 | Japan | 427/3 |
| 1059044 | 2/1967 | United Kingdom | 427/3 |

*Primary Examiner*—Shrive Beck
*Assistant Examiner*—Erma Cameron
*Attorney, Agent, or Firm*—Charles J. Metz

[57] ABSTRACT

A method of highlighting intagliations in white or colored coated tablets by spraying onto said tablets a suspension comprising a filling material having a different color, a waxy material and a solvent, and removing the solvent and the excess of filling material and waxy material.

16 Claims, No Drawings

METHOD OF HIGHLIGHTING INTAGLIATIONS IN TABLETS

CROSS-REFERENCE TO RELATED APPLICATIONS

This application is based upon PCT Application No. PCT/EP92/00358, filed Feb. 14, 1992, which claims priority from European Patent Application Ser. No. EP. 91.200.417.3, filed Feb. 27, 1991.

The present invention relates to a method of highlighting intagliations in tablets by selectively depositing and fixing in said intagliations a filling material having a different color than that of the tablet surface.

As more and more medicines become available, the risk of confusing look-alike or resembling medicines increases. Such poses a potential threat to patients, in particular to the elderly and to those patients taking more than one preparation. A significant aspect of improving drug safety therefore resides in avoiding and eliminating this risk of confusing different preparations.

Besides distinguishing medicines by means of color or shape, the use of inscriptions has become a method of choice for identifying preparations. Inscriptions are particularly attractive due to their versatility in conveying information such as, for example, the company name, product name, the dose and the like identifying marks.

The printing of marks on the surface of tablets is a first approach to identify preparations. Drawbacks associated with this technique are the necessity of using specialized machinery and the low quality of the printed marks due to smearing and smudging.

Another method involves the engraving or impressing of a figure, mark, character or any combination thereof, in a tablet by a punching procedure. Such impressed marks are generally termed 'intagliations' and will henceforth be designated as such.

Unfortunately, said intagliations are not easily discerned as their legibility depends on the irregularities on the surface of the tablets and the quality of the outer coating film which may partially or completely fill up said intagliations. This problem is further aggravated by the increasing tendency towards smaller unit dosage forms.

EP-B-0,060,023 discloses a method of emphasizing intagliations in colored (i.e. not white) solid articles, in particular tablets, by coating the tablet surface and filling up the intagliations with a coating film comprising an optically anisotropic substance. An optical contrast between the tablet surface and the intagliations is obtained, presumably due to the different orientation of the optically anisotropic substance on the tablet surface and in the intagliations. The technique is limited to colored articles and only allows the use of optically anisotropic filling materials. The optical effect merely being based on a different contrast is not particularly clear.

EP-B-0,088,556 relates to a method of highlighting intagliations in white or colored tablets by contacting said tablets with a dry, powdery material having a different color than the tablet surface and then removing the excess powdery material not deposited in the intagliations. The powdery material is taught to adhere better to the intagliations of coated tablets than to those of uncoated tablets. Adherence can further be increased by using a mixture of a wax and a powdery material as the deposition material and heating the filled tablets to 40°-90° C. in order to melt the wax. Finally, an outer coating may be applied to the filled tablets.

The method disclosed in EP-B-0.088,556 has several problems. In the first place it has been found that the adhesion of the powdery material to the intagliations is not satisfactory as said material shows a tendency to loosen and fall out. This problem arises particularly when an outer coating film is applied to the filled tablet and the loosened material becomes fixed in said outer coating film, thus yielding speckled tablets. Addition of a wax to the powdery material in order to improve adhesion on the other hand, adversely affects the distribution of the powdery material in that more of it sticks to the surface of the tablet and is difficult to remove. Several more drawbacks are associated with the use of a wax in the dry powdery material. In particular the necessity to heat the tablets filled with a wax and a powdery material in order to melt said wax, poses a hardly acceptable risk since many medicines are thermolabile and might deteriorate significantly in the process. Further it proves difficult to dye evenly a dry mixture of a wax and a powdery material, which in turn puts a limitation on the effectively possible color combinations.

The method of the present invention differs from the prior method disclosed in E-B-0,088,556 by the fact that an optionally colored filling material and a suitable wax are suspended in a solvent and sprayed onto a coated intagliated tablet. Following the removal of the solvent and the excess deposition material, tablets are obtained having a firmly fixed amount of said deposition material specifically in the intagliations. Said tablets have superior visual attractivity over those obtained using prior art methods due to the complete and specific filling of the intagliations and absence of deposition material on the surface of the tablets. An outer coating film can easily be applied to the thus obtained highlighted intagliated tablets without danger of loosening the deposition material from the intagliation. The present method further avoids high temperatures and thus is amenable for identifying solid preparations comprising thermolabile medicines.

The present invention relates to a method of highlighting intagliations in white or colored coated tablets by spraying onto said tablets a suspension comprising a filling material having a different color, a waxy material and a suitable solvent, and removing the solvent and the excess of filling material and waxy material; and to tablets obtainable by said method.

The tablets used as a substrate preferably are film-coated. Film-coated tablets allow a more selective bonding of the filling material to the intagliations and less adherence to the tablet surface than uncoated tablets because of the reduced porosity of the tablet surface (decreased roughness). Any material generally used for applying a coating film to tablets may be employed. For example, suitable materials are, e.g. methylcellulose, hydroxypropyl methylcellulose, hydroxypropylcellulose. carboxymethylethyl cellulose, cellulose acetate phthalate, hydroxypropyl methylcellulose phthalate, acrylates, copolymers of acrylic and methacrylic acid esters and the like.

The coating films may be plasticized with suitable plasticizers such as, e.g. polyethylene glycol, propylene glycol, glycerol, diethyl phthalate, dibutyl sebacate, citroflex, triacetin and the like. If necessary coloring agents can be added. These can be natural pigments such as talc, kaolin, titanium dioxide, or dyestuffs or lake dyestuff selected from accepted food colors. The coating solvent can be water or any other organic solvent suitable for film-coating such as, for example, an alcohol, e.g. ethanol, 2-propanol, a ketone, e.g. acetone, or a halogenated hydrocarbon, e.g. dichloromethane. Preferably the coating is applied by spraying a solution on the tablets in a peforated side-vented pan (Pellegrini, Accela-Cota ®, Hi-coater ® (HCT-20) by means of a spraying system worked by air pressure. The process conditions are those generally employed in coating procedures provided that due care is taken to avoid filling of the intagliations.

A wide variety of filling materials can be used for the filling of the intagliations. Suitable filling agents are, for example, starches, e.g. corn starch, rice starch, wheat starch, potato starch, preferably corn starch or rice starch; celluloses, e.g. methylcellulose. ethylcellulose, carboxymethylcellulose, hydroxypropylcellulose, hydroxypropyl methylcellulose, hydroxypropyl methylcellulose phthalate, crystalline cellulose, preferably microcrystalline cellulose fibers (Elecma P050 ®); lactose and other sugar or sugar alcohols, e.g. sucrose or mannitol, preferably micronised lactose 200 mesh, spray-dried and micronised lactose (DCL-11 ®) or mannitol; organic acids, e.g. stearic acid, fumaric acid, citric acid, preferably fumaric acid; or inorganic substances, e.g. sodium chloride, calcium carbonate, preferably sodium chloride, all giving white intagliations. Other finely divided filling materials such as titanium oxide, talc, kaolin, magnesium stearate and aluminum lakes in practice are less preferred because of their greater tendency to stick to the surface of tablets. The most preferred filling materials are corn starch and microcrystalline cellulose. Colored intagliations are obtained by previously dyeing the filling material. This is achieved by suspending the filling material in a solution of the dye, filtering off, drying and finally grinding. Starches and celluloses such as cited hereinabove and especially those specifically preferred hereinabove can be dyed in water, with, for example, edible lake pigments, e.g. FD&C blue no. 2, FD&C red no. 3, FD&C yellow no. 6, D&C yellow no 10 and the like or any combinations thereof. The weight to weight ratio of said lake pigments to the filling material generally ranges from 0.1:100 to 10:100 and may be choosen in function of the desired intensity. Water soluble filling materials such as lactose can effectively be dyed by suspending them in a solution of an alcohol-soluble dye such as FD&C red no. 3 or D&C yellow no. 10 in an alcohol such as ethanol.

The optionally colored filling materials are suspended in a solution of a waxy material in a suitable solvent. The waxy material is added to enhance the adherence of the filling materials. Examples of waxy materials are polyethylene glycols, natural waxes such as, e.g. beewax or carnauba wax, hydrogenated oils, higher fatty acids and fatty acid esters, fatty alcohols and polyoxyethylene ethers of fatty alcohols. Preferred waxy materials are polyethylene glycols (PEG), in particular PGE 400, PEG 600, PEG 1000, PEG 1500 and PEG 4000.

The proportion of waxy material to filling materials is a very critical parameter in the filling process. Too little waxy material will lead to insufficient bonding of the filling material; with too much waxy material the filling material will bond too strongly to the tablet surface and consequently will be difficult to remove afterwards.

The weight to weight ratio of the waxy material to filling material may range from about 1:3 to about 1:12, in particular from about 1:4 to about 1:9. For waxes having a low molecular weight and low melting point, e.g., PEG 400, PEG 600, PEG 1000 said ratio preferably ranges from 1:4 to 1:6 and in particular is about 1:5. For waxes having a higher molecular weight and melting point, e.g., PEG 1500, PEG 2000, said ratio preferably ranges from 1:6 to 1:8 and in particular is about 1:7.

Suitable solvents are those solvents wherein the filling material and, if present, the dye, do not dissolve. For example, non-dyed starches and celluloses may be suspended in alcohols, e.g. ethanol, isopropanol and the like, halogenated hydrocarbons, e.g. dichloromethane, trichloromethane and the like. Dyed starches, dyed celluloses and non-dyed lactose may be suspended in water-free alcohols, in particular absolute ethanol. The amount of solvent in the final suspension for spraying onto the coated intagliated tablets may range from about 70% to about 85% (w/w) in particular from about 75% to about 81% (w/w), more in particular from about 77% to 81%.

The filling suspension may be sprayed on the coated tablets in a flow-through type coating pan or in a perforated side-vented pan by means of a spray worked by air pressure. Preferably said suspension is kept at room temperature and is stirred or agitated to prevent sedimentation. The temperature of the tablets within the coating pan is advantageously raised slightly to about 30° to 60° C., in particular 30°–40° C. by employing warm inlet-air.

After applying the amount of filling material required, the spraying process is stopped and the excess of solid material adhering to the tablet surface is removed by blowing off with air, meanwhile keeping the tablets tumbling to rub off the filling material deposited on the tablet surface.

To prevent the loosening of deposited filling material, a thin colorless seal-coating layer can be applied to the tablets. The coating polymer can be one of those mentioned above for the subcoating, especially hydroxypropyl methylcellulose, together with a suitable plasticizer as mentioned hereinabove. In the case of water soluble filling materials or dyes, the solvent used is preferably an organic solvent since water would dissolve the filling material and the dye fixed on the solid filling material. Said seal-coating process may be conducted in any of the usual coating devices such as, for example, flow-through coating pans of side-vented coating pans, employing conventional process conditions.

The tablets obtainable by the aforementioned methods have superior highlighted intagliations and said tablets are meant to constitute an aspect of the present invention.

The different steps involved in the filling and coating processes are described in more detail below by means of examples.

EXPERIMENTAL PART

Example 1 a) 500 g biconvex placebo tablet cores (comprising lactose, corn starch, providone, microcrystalline cellulose, silicone dioxide and magnesium stearate) were put into a Hi-coated ® (HCT-20) flow-through pan and warmed to ±40° C. with air of 60° C. The cores had a diameter of 6.5 mm, a nominal weight of 100 mg and an inscription on one side, the other side being blank. The coating suspension consisted of 12.0 g of hydroxypropyl methylcellulose in 0.1 l of purified water, 2.64 g of propylene glycol (as a plasticizer), 3.6 g of titaniumdioxide, 1.2 g of FD&C blue no. 2 aluminum lake and 2.4 g of talc. The suspension was homogenized for 10 minutes. The tablets were coated using the following parameters:

pan rotation speed : 35 rpm
inlet-air temperature : 67°–70° C.
outlet-air temperature : 37°–40° C.
atomizing air pressure : 0.18 MPa (1.8 bar)
liquid addition rate : 4 g. minutes$^{-1}$ As a result of the coating process there were obtained blue coated tablets.

b) The blue film-coated tablets were put in a Hi-coater ® (HCT-20) flow-through pan and warmed with air of 50° C. while rotating at 40 rpm.

In a solution of 1.5 g of polyethylene glycol 1500 in 50 ml of ethanol there were suspended 10.2 g of corn starch and the whole was homogenized for 10 minutes. The suspension was sprayed on the tablets at a delivery rate of 9 g. minutes$^{-1}$. The tablets were kept tumbling in the rotating pan for another 5 minutes. The excess of filling material deposited on the tablet surface was blown off by atomizing air at 0.2 MPa (2 bar) for 10 minutes while rotating the pan.

As a result there were obtained blue tablets with intagliations highlighted in white.

c) The blue coated tablets were white intagliations were put in the Hi-coater ® (HCT-20) and warmed with air of 65° C. for 5 minutes while rotating at 35 rpm. The seal-coating solution consisted of 5.0 g of hydroxypropyl methylcellulose in 0.050 l of purified water and 1.1 g of propylene glycol as a plasticizer. The tablets were coated using the following conditions:

pan rotation speed : 35 rpm
inlet-air temperature : 65°–70° C.
outlet-air temperature : 36°–40° C.
atomizing air pressure : 0.18 MPa (1.8 bar)
liquid addition rate : 3.5 minutes$^{-1}$ The tablets were kept rotating in the coating pan for another 10 minutes while warming with air of 70° C.

EXAMPLE 2 a) 10 kg of biconvex placebo tablets (comprising lactose, corn starch, hydroxypropyl methylcellulose, microcrystalline cellulose, silicon dioxide and magnesium stearate) were put in an Accela-Cota ® 24 inch flow-through pan and warmed to ±40° C. with air of 60° C. The tablets cores had a diameter of 9 mm and a nominal weight of 230 mg. They were half scored with an $$\frac{Ox}{30}$$

inscription on one side and a JANSSEN inscription on the other. The coating suspension consisted of 190.0 g of hydroxypropyl methylcellulose in 1.9 l of purified water, 60.0 g of propylene glycol (as plasticizer), 110.0 g of titanium dioxide and 48.0 g of talc. The suspension was homogenized for 20 minutes. The tablets were coated using the following parameters:

pan rotation speed : 14 rpm
inlet-air temperature : 55°–60° C.
outlet-air temperature : 40°–42° C.
atomizing air pressure : 0.42 MPa (4.2 bar)
liquid addition rate : 27 g. minutes$^{-1}$ As a result there were obtained white film-coated tablets.

b) The white film-coated tablets were put in the Accela-Cota ® 24 inch side-vented pan and warmed with air of 40°–45° C. while rotating at 14 rpm. 126.0 g of microcrystalline cellulose were colored with FD&C blue no. 2 (1% w/w of MCC) by suspending it in an aq. solution of FD&C blue no. 2 dye, filtering the suspension, vacuum drying the solid at 50° C. and grinding it. The colored microcrystalline cellulose was then suspended in a mixture of 26.0 g of polyethylene glycol 400 and 640 g of ethanol. The whole was homogenized for 20 minutes.

The suspension was sprayed on the tablets using the following parameters:

pan rotation speed : 14 rpm
inlet-air temperature : 40° C.
outlet-air temperature : 30°–35° C.
atomizing air pressure : 0.2 MPa (2.0 bar)
liquid addition rate : 30 g. minutes$^{-1}$ The tablets were kept tumbling in the rotation pan for another 5 minutes. The excess of the deposited solids were removed by blowing atomizing air at 0.4 MPa (4.0 bar) for 5 minutes (inlet-air temperature : 55á60° C.; outlet-air temperature: 40° C.) while rotating at 14 rpm. As a result, there were obtained while film-coated tablets with intagliations highlighted in blue.

c) The white coated tablets with intagliations highlighted in blue were put in the Accela-Cota ® 24 inch coating-pan and warmed with air of 60° C. for 10 minutes. The seal-coating solution consisted of 67.0 g of hydroxypropyl methylcellulose in 1.26 l of purified water and 13.4 g of propylene glycol as plasticizer.

The tablets were coated using the following conditions:

pan rotation speed : 14 rpm
inlet-air temperature : 50°–55° C.
outlet-air temperature : 40°–45° C.
atomizing air pressure : 0.4 MPa (4.0 bar)
liquid addition rate : 23 g. minutes$^{-1}$ The tablets were kept rotating in the coating pan for another 15 minutes while warming with warm air of 60° C.

EXAMPLE 3 a) 29 kg of oblong placebo tablet cores (comprising lactose, corn starch, porridone, microcrystalline cellulose, silicon dioxide and magnesium stearate) were put in a Glatt (type GC-750flow-through coating pan and warmed to about 50° C. with air of about 80° C. The length of the tablet cores was 12.5 mm, the width 5.3 lmm and the nominal weight was 180 mg. The tablet cores had an inscription Ke 20 and a score line on one side and a JANSSEN inscription on the other.

The coating suspension was prepared by dissolving 780 g hydroxypropyl methylcellulose in 6.825 l of purified water, adding 195 g polyethylene glycol 400 (as plasticizer) and homogenizing the solution for 20 minutes.

The tablets were coated using the following parameters:

pan rotation speed : 8 rpm
number of spraying nozzles : 2
diameter of spraying nozzles : 1.2 mm inlet-air temperature : 75°–80° C.
outlet-air temperature : 48°–52° C.
atomizing air pressure : 0.3 MPa (3 bar)
liquid addition rate : 90 g. minutes$^{-1}$ As a result there was obtained white film-coated tablets.

b) The white film-coated tablets in the Glatt (type GC-750) side vented coating pan were rotated at 8 rpm while warming with air of 75°–80° C.

247.5 g of corn starch were colored with FD&C red no. 40 (0.6% w/w of corn starch) by suspending the corn starch in an aqueous solution of FD&C red no. 40, filtering the suspension, vacuum drying the solid at 50° C. and finally grinding it. The colored corn starch was then suspended in a mixture of 10.5 g polyethylene glycol 4000, 42 g polyethyleneglycol 400 and 1200 g of dichloromethane, and was homogenized for 15 minutes.

The suspension was sprayed on the tablets using the following parameters:
pan rotation speed : 8 rpm
number of spraying nozzles : 2
diameter of spraying nozzles : 1.2 mm
inlet-air temperature : 75°–80° C.
outlet-air temperature : 50°–55° C.
atomizing air pressure : 0.25 MPa (2.5 bar)
liquid addition rate : 215 g. minutes$^{-1}$ When all of the suspension was applied, the tablets were kept tumbling in the rotating pan for 20 minutes. The excess of the deposited solids was removed by blowing atomizing at air 0.25 MPa (2.5 bar) at an inlet-air temperature of approximately 75°–80° C. (outlet-air temperature : 60° C.). As a result there were obtained white film-coated tablets with intagliations and the score line highlighted in red.

c) The white film-coated tablets with red intagliations and score line in the Glatt (type GC-750) coating pan were warmed with air of 80° C. for 5 minutes. The seal-coating solution was prepared by dissolving 280 g hydroxypropylmethylcellulose in 2.45 l of purified water, adding 70 g polyethyleneglycol as a plasticizer and homogenizing the solution.

The tablets were coated using the following conditions:
pan rotation speed : 8 rpm
number of spraying nozzles : 2
diameter of spraying nozzles : 1.2 mm
inlet-air temperature : 75°–80° C.
outlet-air temperature : 46°–50° C.
atomizing air pressure : 0.3 MPa (3 bar)
liquid addition rate : 130 g. minutes$^{-1}$ When all of the coating solution had been applied, the tablets were keeping rotating in the coating pan for 10 minutes, meanwhile supplying warm air at an inlet-air temperature of 75°–80° C.

We claim:

1. A method of highlighting intagliations in white or colored coated tablets, characterized by (a) spraying onto said tablets a suspension comprising a filling material having a different color than the surface of said coated tablets, a waxy material and a solvent, (b) removing the solvent, and (c) removing the excess of filling material and waxy material from the entire surface of said tablets except for the intagliations.

2. A method according to claim 1 wherein the filling material is corn starch or microcrystalline cellulose.

3. A method according to claim 2 wherein the filling material is previously dyed with an edible lake pigment.

4. A method according to claim 1 wherein the amount of solvent in the suspension ranges from 70% to 85%.

5. A method according to claim 1 wherein the solvent and the excess of filling material and waxy material are removed by blowing off with air and keeping the tablets tumbling.

6. A method according to claim 1 wherein the waxy material is a polyethylene glycol.

7. A method according to claim 2 wherein the waxy material is a polyethylene glycol.

8. A method according to claim 3 wherein the waxy material is a polyethylene glycol.

9. A method according to claim 6 wherein the weight to weight ratio of waxy material to filling material ranges from 1:3 to 1:12.

10. A method according to claim 7 wherein the weight to weight ratio of waxy material to filling material ranges from 1:3 to 1:12.

11. A method according to claim 8 wherein the weight to weight ratio of waxy material to filling material ranges from 1:3 to 1:12.

12. A method according to claim 1 wherein the solvent does not dissolve the filling material.

13. A method according to claim 2 wherein the solvent does not dissolve the filling material.

14. A method according to claim 3 wherein the solvent does not dissolve the filling material or the dye.

15. A method according to claim 1 wherein the tablets containing the filling material in the intagliations are provided with a further coating film.

16. A tablet produced by the method of claim 1.

* * * * *